(12) United States Patent
Ghosal

(10) Patent No.: US 6,290,996 B1
(45) Date of Patent: Sep. 18, 2001

(54) METHOD OF INHIBITING BLOOD PLATELET AGGREGATION

(75) Inventor: Shibnath Ghosal, Varanasi (IN)

(73) Assignees: Natreon Inc., New Brunswick, NJ (US); Indian Herbs Research & Supply Company LTD, Saharanpur (IN)

( * ) Notice: Subject to any disclaimer, the term of this patent is extended or adjusted under 35 U.S.C. 154(b) by 0 days.

(21) Appl. No.: 09/667,042

(22) Filed: Sep. 21, 2000

Related U.S. Application Data

(63) Continuation-in-part of application No. 09/503,899, filed on Feb. 15, 2000, now Pat. No. 6,235,721, and a continuation-in-part of application No. 09/251,917, filed on Feb. 17, 1999, now Pat. No. 6,124,268.

(51) Int. Cl.$^7$ .................................................. A01N 65/00

(52) U.S. Cl. ........................ 424/777; 424/401; 424/439; 424/440; 424/769; 514/25; 514/27

(58) Field of Search .................... 514/25, 27; 424/769, 424/777, 401, 439, 440

(56) References Cited

PUBLICATIONS

Chemical Abstract 103:27136, "Emblica officinalis reduces serum, aortic and hepatic cholesterol in rabbits" (1985).*

* cited by examiner

*Primary Examiner*—Frederick Krass
(74) *Attorney, Agent, or Firm*—Walter Katz

(57) ABSTRACT

A method of inhibiting blood platelet aggregation in humans which comprises administering an extract blend of the fruit of the Emblica officinalis plant to control said aggregation, suitably in a dose amount of about 50–500 mg/day.

8 Claims, No Drawings

METHOD OF INHIBITING BLOOD PLATELET AGGREGATION

CROSS REFERENCE TO RELATED CO-PENDING U.S. PATENT APPLICATIONS

This application is a continuation-in-part of U.S patent applications Ser. No. 09/251,917, filed Feb. 17, 1999, now U.S. Pat No. 5,124,268 and Ser. No. 09/503,899, filed Feb. 15, 2000, now U.S. Pat. No. 6,235,721 by the same inventor as herein.

BACKGROUND OF THE INVENTION

1. Field of the Invention

This invention relates to inhibiting blood platelet aggregation in humans, and, more particularly, to the use of an extract blend of the fruit of the Emblica officinalis plant for effectively controlling said aggregation.

2. Description of the Prior Art

Cerebral, cardiovascular, inflammatory disorders and geriatric progression represent atheromatous syndromes or vascular aging in humans resulting in progressive hypoxia caused in part by the action free radicals, such as the hemoglobin-oxo-ferryl (IV) radical. This radical induces lipid peroxidation which is implied in the pathophysiology of atherosclerosis. Through a similar mechanism, an alteration of the blood platelet function, promoted by free radicals, causes the formation of thrombi which constitutes the basis of infarction. Antioxidants, such as ascorbic acid (AA), alpha-tocopherol (Vitamin E), and pycnogenols (procyanidins) (U.S. Pat. No. 5,720,956), have been indicated for preventing or inhibiting the harmful effects of hypoxia following atherosclerosis and for surveillance against cardiac and cerebral infarction.

Reactive oxygen species (ROS) in the body also can cause lipid peroxidation of membranes which generate fragments that bind to platelet activating factor (PAF)-receptors on target cells and exert a PAF-like effect, namely, aggregation of blood platelets. ROS also can inactivate PAF-acetyl hydrolase, an enzyme present within plasma lipoproteins, that rapidly destroys PAF.

Certain biochemical agents, e.g. ADP, adrenaline and collagen, that promote PAF-like activity, also can cause lipid peroxidation which results in platelet aggregation. ADP can act via a metallo-complex-ROS system through its potent iron binding capacity, as shown in the equation below:

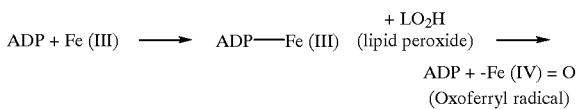

The oxoferryl radical, which is a complex ROS, can cause platelet aggregation in platelet rich plasma (PRP).

Accordingly, it is an object of this invention to provide an improved method of inhibiting induced-blood platelet aggregation in humans which can result in atherosclerosis.

Another object of the present invention is to provide a method of controlling free radical induced pathogenesis which can result in progressive hypoxia.

Still another object herein is to provide a method of inhibiting blood platelet aggregation which may be induced by a reactive oxygen species, such as ADP, adrenaline or collagen, or by human behavior patterns, such as smoking.

A feature of the invention is the provision of a method of inhibiting blood platelet aggregation in humans by administering a dose amount of 50–500 mg/day of an extract blend of the fruit of the Emblica officinalis plant.

Another feature of the invention is the inhibition of blood platelet aggregation by an extract of the Emblica officinalis plant without causing adverse side effects.

Still another feature of the invention is the provision of a pharmaceutical composition which includes about 50–500 mg of the extract blend.

These and other objects and features of the invention will be made apparent from the following more detailed description of the invention.

DETAILED DESCRIPTION OF THE INVENTION

The antagonist for inhibition of blood platelet aggregation in humans according to the invention is an extract blend, hereinafter referred to as "CAPROS™", which is isolated in stable form from the fruit of the Emblica officinalis plant, as described in detail in the aforementioned co-pending patent application. The extraction process includes treating the finely-pulped fruit with a dilute aqueous or alcoholic-water salt solution, e.g. a 0.1 to 5% (w/w) sodium chloride solution, or the like, preferably at about 70° C.±5° C., or with a buffer solution, e.g. 0.1 to 5% (w/w) of sodium citrate/citric acid, or the like, filtering and drying, to provide the extract in powder form.

The CAPROS™ extract includes the active constituents Emblicanin-A and -B, which are gallic/ellagic acid derivatives of 2-keto-glucono-δ-lactone, in an amount, by weight, of about 35–55%; as well as Punigluconic acid, or 2,3-di-O-galloyl-4,6(S)-hexahydroxydiphenoyl gluconic acid (about 4–15%); Pedunculagin, or 2,3,4,6-bis-(S)-hexahydroxydiphenoyl-D-glucose (about 10–20%); Rutin, or flavanol-3-glycoside or 3',4',5,7-tetrahydroxyflavone-3-)-rhamnoglucoside (about 5–15%); and low-to-medium molecular weight tannoids of gallic/ellagic acid (about 10–30%); gallic acid (about 0–5%) and ellagic acid (about 0–5%).

The invention will now be described in more detail with reference to the following experimental results.

INHIBITION OF BLOOD PLATELET AGGREGATION EXAMPLE 1

A male mongrel dog weighing about 10 kg, was anesthetized with sodium pentobarbitone (35 mg/kg, i.v.). The venous blood was collected and mixed with one-tenth volume of a sodium citrate solution (3.8%, w/v) to prevent clotting. The thus-protected blood was centrifuged at 220×g for 20 min to obtain a supply of platelet rich plasma (PRP).

A sample of 3 ml of PRP was pipetted into a cuvette and its optical density (o.d.) was measured at 600 nm at room temperature (25°±2° C.). The dark current was set at infinity and the optical density of distilled water at zero. Additions of the test inhibition material and aggregation inducer to the PRP were made while it was being stirred. The optical density of the test solution was measured continuously and recorded every 5 minutes.

Blood platelet aggregation was induced from the PRP by ADP or adrenaline, as described in the paper by Bom, G. V. R., "Aggregation of Blood Platelets by Adenosine and its Reversal", Nature 194, 927–929 (1962).

Table 1 below sets forth the experimental results obtained when a series of test inhibition samples were added to the PRP and aggregation induced by ADP or adrenaline.

TABLE 1

| Test Material | Dose ($\mu$M) | % Inhibition of Blood Platelet Aggregation | |
|---|---|---|---|
| | | ADP-Induced | Adrenaline-Induced |
| Ascorbic acid | 5.0 | 14.2 ± 1.7 | nil |
| | 10.0 | 32.4 ± 4.4 | nil |
| | 20.0 | 45.1 ± 6.6 | 7.2 |
| Pycnogenols* | 5.0 | 15.8 ± 2.2 | nil |
| | 10.0 | 40.4 ± 4.3 | 12.4 ± 2.8 |
| CAPROS ™** | 1.0 | 16.2 ± 2.8 | 11.8 ± 2.0 |
| | 2.5 | 55.1 ± 5.4 | 42.4 ± 3.0 |
| | 5.0 | 72.8 ± 7.1 | 62.7 ± 5.5 |
| CAPROS ™ + | 2.5 + 5.0 | 69.8 ± 5.7 | 58.1 ± 4.3 |
| Ascorbic acid | 5.0 + 5.0 | 78.7 ± 5.0 | 66.1 ± 6.6 |

*Molarity calculated on the basis of dimeric procyanidine(s)
**Values are mean ± SEM (n = 6 to 10)

The results above demonstrate that CAPROS ™ alone, or with ascorbic acid, inhibits aggregation of platelets significantly more effectively than either the ascorbic acid or pycnogenols samples, even at a lower dose than the materials. Furthermore, enhanced inhibition of platelet aggregation by CAPROS™ was effected without causing any adverse side effects such as bleeding or allergic reactions, which was common with the other test materials.

EXAMPLE 2

Inhibition of blood platelet aggregation by CAPROS® was also studied by the method of Choi, H. Y. et al, "Modified Smear Method for Screening of Potential Inhibitors of Platelet Aggregation from Plant Sources", J. Nat. Prod. 48, 363–370 (1985).

Experimental Procedure

Rats (200±30 g) were anesthetized with chloroform and blood was drawn from the heart into a plastic syringe containing one-tenth volume of 2.2% trisodium citrate. The citrated blood was then centrifuged at 200×g for 10 min at room temperature to provide a platelet rich plasma (PRP) as a supernant liquid.

Water soluble test samples of the aggregating agent were dissolved in a saline solution (0.15 N NaCl) to give the following final concentrations: adenosine-5'-diphosphate (ADP) $1 \times 10^{-6}$ g/ml; and collagen $6 \times 10^{-6}$ g/ml. A solution of the test sample (0.02 ml), at different concentrations, was added to 0.16 ml of PRP and mixed. Two minutes after incubation at 37° C. for collagen, or at room temperature (25±2° C.) for ADP, 0.02 ml of the test aggregating agent (or saline as the control) was added and the tube was vigorously agitated for 10 sec. Thin smears were prepared on glass slides after 6 min incubation at 37° C. for collagen; and after 4 min at room temperature for ADP. The test slides then were dried quickly in air; and the smears were fixed in ethyl alcohol, treated with Wright stain, washed and dried. The test smears then were subjected to examination under an ordinary light microscope using an oil immersion objective lens (1000×).

The degree of PRP-aggregation was graded as follows: (−)no aggregation e.g. PRP plus saline (control); (±) slight aggregation; (+) minor aggregation: (++) major aggregation, as observed with collagen or ADP; and (+++) a stronger aggregation than any of the above. 0.1 mg/ml of aspirin was used to prevent aggregation due to ADP; and 250 $\mu$g/ml of aspirin was used to prevent aggregation by collagen.

CAPROS™ at three different concentrations (50, 100 and 200 $\mu$g/ml) was tested to determine its anti-aggregating effect against ADP and collagen. At 200 $\mu$g/ml, CAPROS™ reduced a (++) platelet aggregating effect to a (−) level; and, at a 100 $\mu$g/ml concentration, it reduced the extent of aggregation to a (±) level against both ADP and collagen. At 50 $\mu$g/ml, it reduced the effects of both ADP and collagen (++), to a (+) level.

The advantageous results achieved by CAPROS™ was unaffected by prolonged storage at room temperatures, while other anti-aggregating agents, such as pycnogenol, lost their antioxidant activity upon standing due to polymerization effects under ordinary conditions.

In practice, the extract blend of the invention is administered in the form of a pharmaceutical use composition which may be a tablet, capsule, syrupielixir, gel and the like, in which the extract blend is present in an amount of about 50–500 mg as a daily dose for humans. Other antioxidants such as ascorbic acid, tocopherols, pycnogenols, glutathione and the like may be included, if desired.

While the invention has been described with particular reference to certain embodiments thereof, it will be understood that changes and modifications may be made which are within the skill of the art. Accordingly, it is intended to be bound only by the following claims, in which:

What is claimed is:

1. A method of inhibiting blood platelet aggregation in humans which comprises administering an extract blend of the fruit of the Emblica officinalis plant to control said aggregation.

2. A method according to claim 1 wherein said extract blend is administered in a dose amount of about 50–500 mg/day.

3. A method according to claim 1 wherein said blood platelet aggregation is induced by a reactive oxygen species, ADP, adrenaline or collagen.

4. A method according to claim 1 wherein said extract blend includes Emblicanin-A and B.

5. A method according to claim 4 wherein said extract blend comprises, by weight, (1) and (2) about 35–55% of the gallic/ellagic acid derivatives of 2-keto-glucono-δlactone; (3) about 4–15% of 2,3-di-O-galloyl-4,6-(S)-hexahydroxydiphenoylgluconic acid; (4) about 10–20% of 2,3,4,6-bis-(S)-hexahydroxydiphenoyl-D-glucose; (5) about 5–15% of 3',4',5,7-tetra-hydroxyflavone-3-O-rhamnoglucoside; and (6) about 10–30% of tannoids of gallic/ellagic acid.

6. A method according to claim 4 in which said extract blend also includes about 0–5% gallic acid and 0–5% ellagic acid.

7. A method according to claim 1 wherein said extract blend is included in a mixture with one or more antioxidants.

8. A method according to claim 6 wherein said antioxidant is ascorbic acid, tocopherol or pycnogenol.

* * * * *